(12) United States Patent
Crouch et al.

(10) Patent No.: US 7,038,444 B2
(45) Date of Patent: May 2, 2006

(54) SYSTEM AND METHOD FOR IN-LINE STRESS MEASUREMENT BY CONTINUOUS BARKHAUSEN METHOD

(75) Inventors: Alfred E. Crouch, San Antonio, TX (US); Gary L. Burkhardt, Adkins, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/708,436

(22) Filed: Mar. 3, 2004

(65) Prior Publication Data
US 2004/0183528 A1   Sep. 23, 2004

Related U.S. Application Data

(60) Provisional application No. 60/320,023, filed on Mar. 19, 2003.

(51) Int. Cl.
*G01N 27/72* (2006.01)

(52) U.S. Cl. .......................... 324/220; 324/209; 73/592

(58) Field of Classification Search ................ 324/219, 324/220, 228, 209, 235, 238, 240; 73/592, 73/598, 600, 622, 623, 643
See application file for complete search history.

(56) References Cited

U.S. PATENT DOCUMENTS 4,408,160 A * 10/1983 King et al. .................. 324/209
6,009,756 A * 1/2000 Willems et al. ............... 73/643

OTHER PUBLICATIONS

Mandal et al., The effects of defect depth and bending stress on magnetic Barkhausen noise and flux-leakage signals, J. Phys. D: Appl. Phys, 30, 1997, pp. 1976-1983.*
Crouch et al., In-Line Stress Measurement by the Continuous Barkhausen Method, Proceedings of IPC 2004, IPC 04-0233, Oct. 4-8, 2004, pp. 1-7.*

* cited by examiner

*Primary Examiner*—Jay Patidar
(74) *Attorney, Agent, or Firm*—Taylor Russell & Russell, PC (57) ABSTRACT

A method and system for performing in-line measurement of stresses in pipeline walls by continuous Barkhausen method comprises an inspection pig including permanent or DC electromagnets for generating a magnetic field that moves with the inspection pig through a pipeline, inductive or other types of magnetic field sensors for reading Barkhausen noise signals generated by the moving magnetic field, and associated instrumentation for amplifying, filtering, detecting and storing the Barkhausen noise signals. The size of the sensors may be selected to match the size of defects being investigated. By comparing trending data over time to determine changes in Barkhausen noise levels, greater detection sensitivity may be achieved. The method may be particularly advantageous for use in inspection pigs that also use magnetic flux leakage to determine pipeline defects, since the magnetic flux leakage method also use permanent or DC electromagnets.

30 Claims, 4 Drawing Sheets

SYSTEM AND METHOD FOR IN-LINE STRESS MEASUREMENT BY CONTINUOUS BARKHAUSEN METHOD

CROSS REFERENCE TO RELATED APPLICATIONS

This application claims benefit of U. S. Provisional Application No. 60/320,023, filed on Mar. 19, 2003.

BACKGROUND OF INVENTION

The invention relates generally to nondestructive methods for measuring stress in ferromagnetic material caused by deformed regions or pressure exerted on the surface of the material. More particularly, the invention is a system and method that relies on the Barkhausen effect to measure properties in regions of ferromagnetic materials that are subjected to various types of stress. While most applications of the Barkhausen effect rely on a time-varying magnetic field to excite the magnetic domains that generate Barkhausen noise in a ferromagnetic material, the present invention relies on a moving, steady state magnetic field generated by a permanent magnet or electromagnet excited by a DC current to create Barkhausen magnetic transitions.

Measurement and characterization of stress and material loss due to erosion, corrosion and gouging in pipelines are critical to early detection of impending failure in order to prevent a situation that is dangerous or destructive to personnel, wildlife or the environment. These concerns have created an increased need to detect and measure anomalous regions of pipe wall stress and strain. Pipelines are subjected to continuous stress from the pressure maintained within the pipeline required to move the pipeline contents through the pipeline. Some pipelines are also subject to ground settlement or movement that may put the pipe wall in a high-stress condition. Bends in a pipe also create stress that varies around the circumference of the pipe. Mechanically damaged areas, such as dents and gouges, have been shown to contain plastically deformed zones, and detection of these zones is a means for identifying mechanical damage. These mechanical defects create residual stress on the pipe inner surface. Once pipelines are installed, they are expected to provide safe and reliable operation over several decades. In addition, inspection and detection of metal loss and stress in long pipelines is more difficult where the pipelines are buried underground or are positioned on an ocean floor.

The most widely used method for in-line inspection and measurement of internal and external material loss in a pipeline wall is magnetic flux leakage (MFL) detection implemented in an inspection pig. Pumping an electronically instrumented MFL inspection pig through a pipeline from one compressor station to the next provides for in-line inspection of the pipeline. The MFL inspection pig may contain a circumferential array of MFL detectors embodying strong permanent or DC electromagnets to magnetize the pipe wall to near saturation flux density. As the inspection pig moves through the pipeline, metal loss, such as corrosion pits, cause an increase in magnetic flux density outside of the pipe material near the corrosion pits that may be detected by Hall effect sensors or induction coils. While the MFL inspection pig has proved effective in detecting surface defects, it lacks an effective means for determining stress in pipe walls. Several other technologies have been developed to determine stress in steel parts such as pipe walls, including a magnetically induced velocity change (MIVC) method, a non-linear harmonics (NLH) method, x-ray diffraction, ultrasonic velocity measurements, and an a-c magnetic bridge.

The MIVC method depends on the change in ultrasonic velocity through steel as the magnetic field in the steel is changed. This method is not practical for in-line measurements, because it requires that the sensor be stationary on the surface of the steel part while the magnetic field is varying. An advantage of the MIVC method is that it can measure biaxial stress as an average value through the wall thickness as opposed to most other methods that respond only to the surface conditions. This method is capable of resolving the stress vector direction by making measurements in two orthogonal directions.

The NLH method has been used with some success to detect mechanical damage in pipelines. Since permeability and other magnetic properties change with both elastic and plastic stress and strain, the output of a NLH sensor will also change with these properties. The NLH method works in an operating pipeline at typical pig speeds, has reasonable sensitivity, and the data is not difficult to analyze. However, the method suffers from lift-off effects, requires a-c excitation, and requires complex instrumentation for operation.

The other methods for determining stress in steel parts, including x-ray diffraction, ultrasonic velocity measurements, and an a-c magnetic bridge require relatively complex instrumentation. Of these methods, only the magnetic bridge is suitable for in-line use, but its deployment for full pipe coverage requires many complex sensing circuits.

Means for determining locations of pipeline wall stress are well known in the relevant art and have been in use for at least 35 years. These means include various configurations of odometer wheels for determining locations of defects in a pipeline, as well as feature recognition by sensors in a pipeline pig that are able to detect pipeline characteristics, such as pipeline girth welds, weld spacing, valves, taps, and branch connectors that are often documented on pipeline maps. Odometer wheels of precisely known diameters are attached to a pig and roll on the inner pipe surface. The wheels may contain sensors, such as magnetic pulsers or optical encoders that produce data related to the wheel angular rotation. The data from these sensors and corresponding pipeline wall defect data are recorded by the pipeline pig. Subsequent playback of the data produces distance information (length of pipeline from launch point) correlated to the defect information. All inspection pig vendors use odometer wheels of similar design. The use of pipeline feature recognition and odometer wheels for distance measurement is common knowledge in the pipeline inspection business and all vendors have used these tools for many years.

Current methods for detection of mechanical damage in pipelines rely on secondary effects such as the effect of the strained area on magnetic flux leakage or the inference of plastic strain from deformation measurements. The Barkhausen method provides a more direct indication of plastically deformed regions of a pipe wall.

SUMMARY OF INVENTION

The present invention provides a system and method for in-line stress measurement that makes use of the permanent or DC electromagnets in an inspection pig to cause Barkhausen magnetic transitions for detection as the inspection pig moves through a pipeline. While previous Barkhausen methods have used an a-c magnetic excitation field and inductive sensors that respond to Barkhausen transitions in ferromagnetic materials, this continuous Barkhausen (CB) method does not require an a-c magnetic excitation field, relying instead on field transitions generated in a pipeline wall by permanent magnets or DC electromagnets positioned in an inspection pig as it moves through the pipeline. The present invention, using the continuous Barkhausen method, may be implemented on an inspection pig containing permanent or DC electromagnets to generate Barkhausen magnetic transitions as the pig moves through a pipeline. In addition, all MFL inspection pigs in use today, whether using permanent magnets or electromagnets, are creating Barkhausen noise as they move through the pipeline. When implemented on MFL inspection pigs, since they already incorporate permanent magnets or DC electromagnetics, the only requirement of the present invention for using those Barkhausen noise signals is to provide suitable sensors, filters and amplifiers for recording the signals, and to develop procedures to interpret the recorded data.

However, there are numerous differences between an inspection pig that uses MFL techniques and an inspection pig that uses Barkhausen noise techniques. For example, MFL techniques are useful for detecting corrosion and erosion of pipeline materials, but are not well suited for measurement of stresses in pipeline walls, where Barkhausen techniques excel. Sensors for use with MFL techniques are positioned between the magnetic poles of the magnets that produce the magnetic field where the magnetic field is uniform, whereas sensors for use with Barkhausen noise techniques are positioned near the magnetic poles of the magnets that produce the magnetic field where there is a strong magnetic field gradient. The filters used with Barkhausen noise techniques also have a higher frequency bandwidth than those for use with MFL techniques. Since Barkhausen noise signal amplitude is typically much lower than magnetic flux leakage signal amplitude, the detectors and amplifiers used with Barkhausen techniques require greater sensitivity.

In general, Barkhausen noise analysis is based on a concept of inductive measurement of a noise-like signal that is generated when a magnetic field is applied to a ferromagnetic sample. A German scientist, Professor Heinrich Barkhausen, first explained the nature of this phenomenon in the year 1919. Today, it is well known that in ferromagnetic materials, the atomic moments are strongly aligned within small regions called magnetic domains. Within each domain, the material is magnetically saturated. However, the direction of the domain magnetization varies from one domain to the next, so that the magnetization of the specimen, as a whole, is ordinarily lower than the saturation value. Changes in bulk magnetization of the specimen take place by movements of the mobile boundaries (domain walls) between adjacent magnetic domains and by creation and annihilation of domains. In general, these domain processes do not take place smoothly, but rather in abrupt, discontinuous jumps. This is called the Barkhausen effect. Details of the Barkhausen effect are strongly influenced by various parameters of the specimen material, and in particular, the state of mechanical stress. This is the basis for using the Barkhausen effect as a method for measuring stress in a ferromagnetic sample, such as a pipeline.

As an alternative to the standard method of applying a time-varying magnetic excitation field to a specimen to produce Barkhausen noise, the continuous Barkhausen method is based on the concept of changing the specimen magnetization in successive local regions by physically moving a magnet, which produces a steady state magnetic field, in the vicinity of the specimen. As the magnet physically moves over each successive local region, that region experiences a time-varying magnetic field that re-aligns the magnetic domains and thus produces Barkhausen noise. A suitable magnetic field sensor that is placed in a fixed orientation to the magnet detects the Barkhausen noise. When implemented on an inspection pig, a moving steady state magnetic field produces Barkhausen noise as the inspection pig moves through the pipeline. By detecting, conditioning, recording and interpreting this noise in relation to a position of the inspection pig, stresses in the pipe wall may be determined. By configuring sensors and DC magnets in an instrumented pig, stress in a pipe wall due to land settling or shifting, pipe bends, and mechanical damage defects may be located and evaluated.

An embodiment of the present invention is a method for in-line measurement by continuous Barkhausen noise detection, comprising the steps of creating one or more magnetic fields circumferentially positioned in a pipeline wall aligned and moving parallel with an axis of the pipeline, sensing Barkhausen noise signals at one or more surfaces of the pipeline wall in one or more transition zones created at an outside fringe of the one or more magnetic fields where there are strong magnetic field gradients, amplifying, filtering, detecting, multiplexing and storing the sensed Barkhausen noise created by the moving magnetic fields, and analyzing and interpreting the stored Barkhausen noise signals in relation to corresponding positions of the inspection pig within the pipeline for determining stress magnitude and corresponding locations of stress in the pipeline wall. The step of creating one or more magnetic fields may comprise positioning one or more magnets each having a north pole and a south pole on the circumference of a cylindrically-shaped inspection pig movably contained within a pipeline, aligning one or more magnetic fields produced by the one or more magnets for producing magnetic fields in a wall of the pipeline parallel to a longitudinal axis of the inspection pig and the pipeline, and moving the inspection pig along the longitudinal axis of the pipeline. The step of sensing Barkhausen noise signals may comprise locating one or more magnetic sensors at transition zones adjacent to the poles of the one or more magnets where there are strong magnetic field gradients in the pipeline wall for detecting Barkhausen noise in the pipeline wall. The step of amplifying, filtering, detecting, multiplexing and storing may comprise connecting the one or more magnetic noise sensors to instrumentation circuits in an instrumentation pack contained within the inspection pig, and sensing Barkhausen noise signals for determining stress in the pipeline wall and storing the noise signals in the instrumentation pack as the inspection pig is caused to transit the pipeline along the longitudinal axis of the pipeline. The step of positioning one or more magnets may be selected from the group consisting of positioning one or more permanent magnets and positioning one or more DC electromagnets magnets energized by a battery pack. The method may further comprise the step of generating Barkhausen magnetic transitions in the transition zones in the pipeline wall as the inspection pig is caused to transit the pipeline. The step of positioning one or more magnets may further comprise positioning one or more magnets in close proximity to a wall of the pipeline. The step of locating one or more magnetic sensors may further comprise locating a multitude of small magnetic sensors for detecting small areas of pipe wall stress. The step of locating one or more magnetic sensors may further comprise locating a small number of large magnetic sensors providing improved signal-to-noise ratios for detecting large areas of pipe wall stress. The step of locating one or more magnetic sensors may further comprise locating one or more magnetic sensors over a radial angle of from 45 to 90 degrees of the circumference of the inspection pig for detecting only stresses due to bends in the pipeline wall. The method may further comprise the step of enhancing detection of pipeline stress by making trending measurements of stored Barkhausen noise signals over a period of time for providing higher detection sensitivity than single absolute measurements of Barkhausen noise signals. The step of connecting the one or more magnetic noise sensors may comprise connecting the one or more magnetic noise sensors to input terminals of one or more amplifiers in the instrumentation pack, connecting output terminals of the one or more amplifiers to input terminals of one or more filters in the instrumentation pack, connecting output terminals of the one or more filters to input terminals of one or more detector circuits in the instrumentation pack, connecting output terminals of the one or more detector circuits to input terminals of a multiplexer in the instrumentation pack, and connecting an output terminal of the multiplexer to a data storage device in the instrumentation pack for storing multiplexed Barkhausen noise data. The steps of positioning one or more magnets and aligning one or more magnetic fields may be included in an existing MFL inspection pig.

Another embodiment of the present invention is a system for in-line measurement by continuous Barkhausen noise detection, comprising means for creating one or more magnetic fields circumferentially positioned in a pipeline wall aligned and moving parallel with an axis of the pipeline, means for sensing Barkhausen noise signals at one or more surfaces of the pipeline wall in one or more transition zones created at an outside fringe of the one or more magnetic fields where there are strong magnetic field gradients, means for amplifying, filtering, detecting, multiplexing and storing the sensed Barkhausen noise created by the moving magnetic fields, and means for analyzing and interpreting the stored Barkhausen noise signals in relation to corresponding positions of the inspection pig within the pipeline for determining stress magnitude and corresponding locations of stress in the pipeline wall. The means for creating one or more magnetic fields may comprise one or more magnets each having a north pole and a south pole positioned on the circumference of a cylindrically-shaped inspection pig movably contained within a pipeline, one or more magnetic fields produced by the one or more magnets for producing magnetic fields in a wall of the pipeline aligned parallel to a longitudinal axis of the inspection pig and the pipeline, and means for moving the inspection pig along the longitudinal axis of the pipeline. The means for sensing Barkhausen noise signals may comprise one or more magnetic sensors located at transition zones adjacent to the poles of the one or more magnets and outside the one or more magnetic fields where there are strong magnetic field gradients in the pipeline wall for detecting Barkhausen noise in the pipeline wall. The means for amplifying, filtering, detecting, multiplexing and storing may comprise one or more magnetic noise sensors connected to instrumentation circuits in an instrumentation pack contained within the inspection pig, and Barkhausen noise signals sensed for determining stress in the pipeline wall and stored in the instrumentation pack as the inspection pig is caused to transit the pipeline along the longitudinal axis of the pipeline. The means for positioning one or more magnets may be selected from the group consisting of means for positioning one or more permanent magnets and means for positioning one or more DC electromagnets magnets energized by a battery pack. The system may further comprise the one or more magnets for generating Barkhausen magnetic transitions in the transition zones in the pipeline wall as the inspection pig is caused to transit the pipeline. The one or more magnets may be positioned in close proximity to a wall of the pipeline. The one or more magnetic sensors may further comprise a multitude of small magnetic sensors for detecting small areas of pipe wall stress. The one or more magnetic sensors may further comprise a small number of large magnetic sensors providing improved signal-to-noise ratios for detecting large areas of pipe wall stress. The one or more magnetic sensors may further comprise one or more magnetic sensors located over a radial angle of from 45 to 90 degrees of the circumference of the inspection pig for detecting only stresses due to bends in the pipeline wall. The system may further comprise enhanced detection by trending measurements of stored Barkhausen noise signals over a period of time for providing higher detection sensitivity than single absolute measurements of Barkhausen noise signals. The one or more magnetic noise sensors connected to the instrumentation circuits may comprise the one or more magnetic noise sensors connected to input terminals of one or more amplifiers in the instrumentation pack, output terminals of the one or more amplifiers connected to input terminals of one or more filters in the instrumentation pack, output terminals of the one or more filters connected to input terminals of one or more detector circuits in the instrumentation pack, output terminals of the one or more detector circuits connected to input terminals of a multiplexer in the instrumentation pack, and an output terminal of the multiplexer connected to a data storage device in the instrumentation pack for storing multiplexed Barkhausen noise data. The positioned one or more magnets and aligned one or more magnetic fields may be included in an existing MFL inspection pig.

Yet another embodiment of the present invention is a system for in-line stress measurement by continuous Barkhausen noise detection, comprising an MFL inspection pig including means for creating one or more magnetic fields circumferentially positioned in a pipeline wall aligned and moving parallel with an axis of the pipeline as the MFL inspection pig transits the pipeline, means for sensing Barkhausen noise signals at one or more surfaces of the pipeline wall in one or more transition zones created at an outside fringe of the one or more magnetic fields where there are strong magnetic field gradients created by the MFL inspection pig, means for amplifying, filtering, detecting, multiplexing and storing the sensed Barkhausen noise created by the moving magnetic fields of the MFL inspection pig, and means for analyzing and interpreting the stored Barkhausen noise signals in relation to corresponding positions of the MFL inspection pig within the pipeline for determining stress magnitude and corresponding locations of stress in the pipeline wall. The MFL inspection pig may comprise one or more magnets each having a north pole and a south pole positioned on the circumferential surface of the MFL inspection pig movably contained within a pipeline, one or more magnetic fields produced by the one or more magnets for producing magnetic fields in a wall of the pipeline aligned parallel to a longitudinal axis of the MFL inspection pig and the pipeline, and means for moving the MFL inspection pig along the longitudinal axis of the pipeline. The means for sensing Barkhausen noise signals may comprise one or more magnetic sensors located at transition zones adjacent to the poles of the one or more magnets where there are strong magnetic field gradients in the pipeline wall for detecting Barkhausen noise in the pipeline wall, the means for amplifying, filtering, detecting, multiplexing and storing may comprise one or more magnetic noise sensors connected to instrumentation circuits in an instrumentation pack contained within the MFL inspection pig, and the Barkhausen noise signals may be sensed for determining stress in the pipeline wall and may be stored in the instrumentation pack as the MFL inspection pig is caused to transit the pipeline along the longitudinal axis of the pipeline. The system may further comprise enhanced detection by trending measurements of stored Barkhausen noise signals over a period of time for providing higher detection sensitivity than single absolute measurements of Barkhausen noise signals.

BRIEF DESCRIPTION OF DRAWINGS

These and other features, aspects and advantages of the present invention will become better understood with regard to the following description, appended claims, and accompanying drawings wherein:

DETAILED DESCRIPTION

Figure 1:
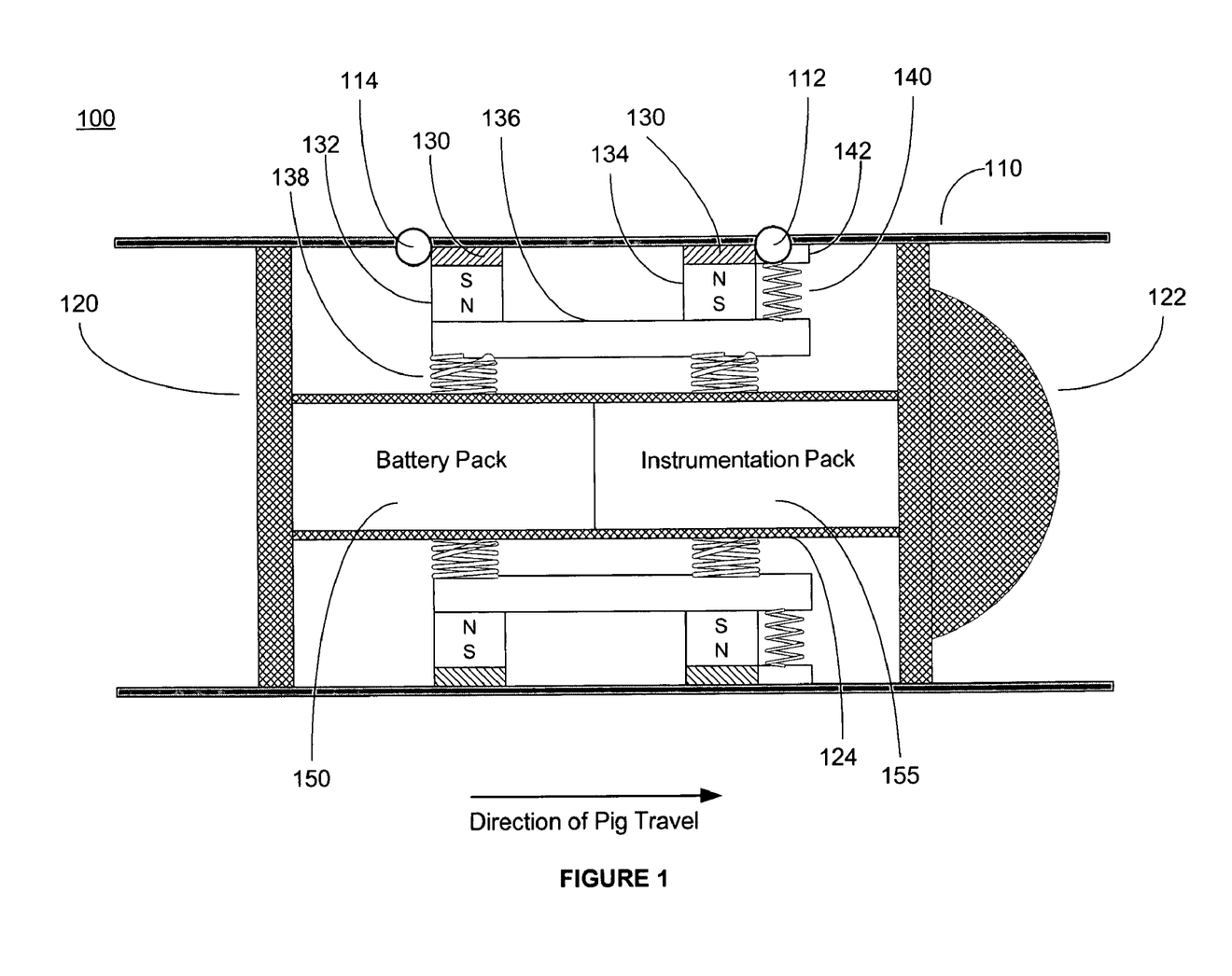
FIG. 1 shows an axial cross-section of an embodiment of the present invention that makes use of permanent magnets.

Turning now to FIG. 1, FIG. 1 shows an axial cross-section of an embodiment of the present invention 100 that makes use of permanent magnets 132, 134. The embodiment comprises an inspection pig 100 movably positioned within a pipe 110. The inspection pig structure consists of a front section 122 connected to a rear section 120 by a center section 124, which houses a battery pack 150 and instrumentation pack 155. A plurality of magnetic field producing assemblies are radially positioned about the center section 124. Each magnetic field producing assembly comprises a first magnet 132 having a first pole connected to a wall of a pipe 110 by a ferromagnetic brush 130. A second pole of the first magnet 132 is connected to an end of a ferromagnetic connector 136. A second magnet 134 has a first pole connected to an end of the ferromagnetic connector 136 opposite the connected second pole of the first magnet 132. A second pole of the second magnet 134 is connected to the wall of the pipe 110 by a ferromagnetic brush 130. The first magnet 132 and the second magnet 134 are identical, but are positioned such that the first pole of the first magnet 132 connected to the brush 130 has an opposite polarity to the second pole of the second magnet 134 connected to the brush 130. This magnetic field producing assembly is held in a position by springs 138, such that the brushes 130 remain in close proximity or contact with the pipe wall 110 to establish a magnetic field in the pipe wall 110 in a region between brushes 130. The magnetic field producing assemblies shown in FIG. 1, comprising the brushes 130, permanent magnets 132, 133, ferromagnetic connector 136 and springs 138 already exist in many MFL inspection pigs already in use. Thus, it would require only detectors and associated instrumentation to implement the present continuous Barkhausen method in these MFL inspection pigs. The magnetic state of the pipe wall in front of the magnetic field producing assemblies nearest the inspection pig front section 122 and behind the magnetic field producing assemblies nearest the inspection pig rear section 120 are in a lower magnetic state than the region of the pipe wall 110 between the brushes 130. The greatest gradient or change in the magnetic field intensity is in transition zones 112, 114 directly in front of each magnetic field producing assembly 112 and directly in back of each magnetic field producing assembly 114. It is in these transition zones 112, 114 where a magnetic field is changing direction and magnitude the produces the greatest magnetic domain movement resulting in peak Barkhausen noise levels. The Barkhausen noise is detected by an inductive or other type of magnetic field sensor 142 positioned by a spring 140 in a vicinity of the transition zones 112 or 114 in the pipe wall 110. FIG. 1 depicts the magnetic field sensor 142 positioned in the vicinity of the front transition zone 112. As the inspection pig moves through the pipeline, the transition zones 112, 114 also move with the inspection pig to produce Barkhausen noise in an axial direction of the pipeline due to movement of the inspection pig. By detecting, conditioning, recording and interpreting this noise in relation to a position of the inspection pig in a pipeline wall, stresses in the pipe wall 110 may be determined.

Figure 2:
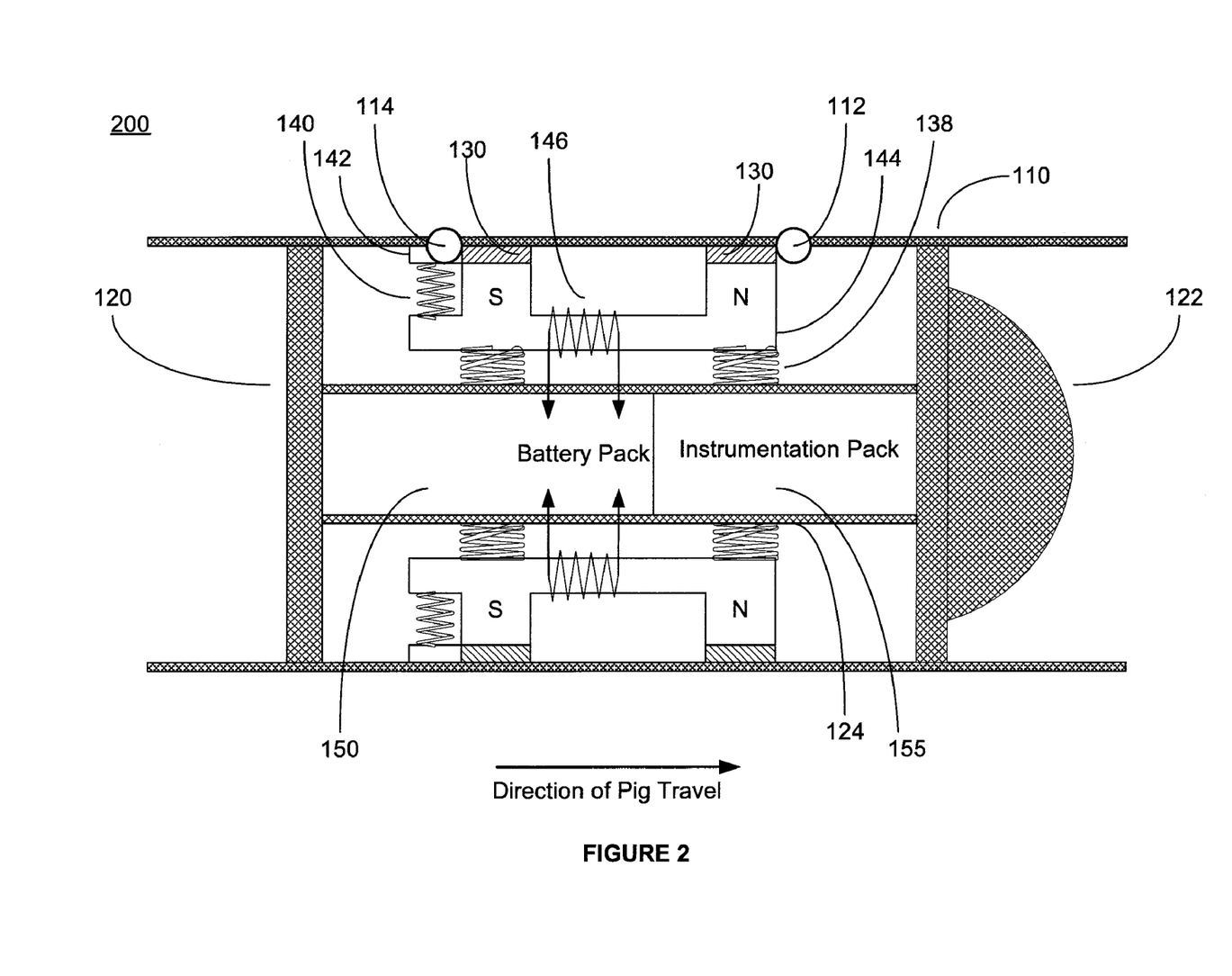
FIG. 2 shows an axial cross-section of an embodiment of the present invention that makes use of DC electromagnets.

Turning now to FIG. 2, FIG. 2 shows an axial cross-section of an embodiment of the present invention 200 that makes use of DC electromagnets 144. The configuration shown in FIG. 2 is similar to that shown in FIG. 1 except that electromagnet 144 excited by a coil 146 connected to a battery pack 150 shown in FIG. 2 replaces the permanent magnets 132, 134 and the ferromagnetic connector 136 shown in FIG. 1. Poles of the electromagnet 144 are magnetically coupled to the pipe wall 110 by brushes 130 to produce transition zones 112, 114, as described in FIG. 1. The electromagnet 144 is positioned by springs 138 such that the brushes 130 remain in contact with the pipe wall 110. The magnetic field producing assemblies shown in FIG. 2, comprising the brushes 130, electromagnet 144, coil 146 and springs 138 already exist in many MFL inspection pig already in use. Thus, it would require only detectors 142 and associated instrumentation to implement the present continuous Barkhausen method in these MFL inspection pigs. As in FIG. 1, the Barkhausen noise is detected by an inductive or other type of magnetic field sensor 142 positioned by a spring 140 in a vicinity of the transition zones 112 or 114 in the pipe wall 110. FIG. 2 depicts the magnetic field sensor 142 positioned in the vicinity of the rear transition zone 114. As the inspection pig moves through the pipeline, the transition zones 112, 114 also move with the inspection pig to produce Barkhausen noise in an axial direction of the pipeline due to movement of the inspection pig. By detecting, conditioning, recording and interpreting this noise in relation to a position of the inspection pig in a pipeline, stresses in the pipe wall 110 may be determined.

Figure 3:
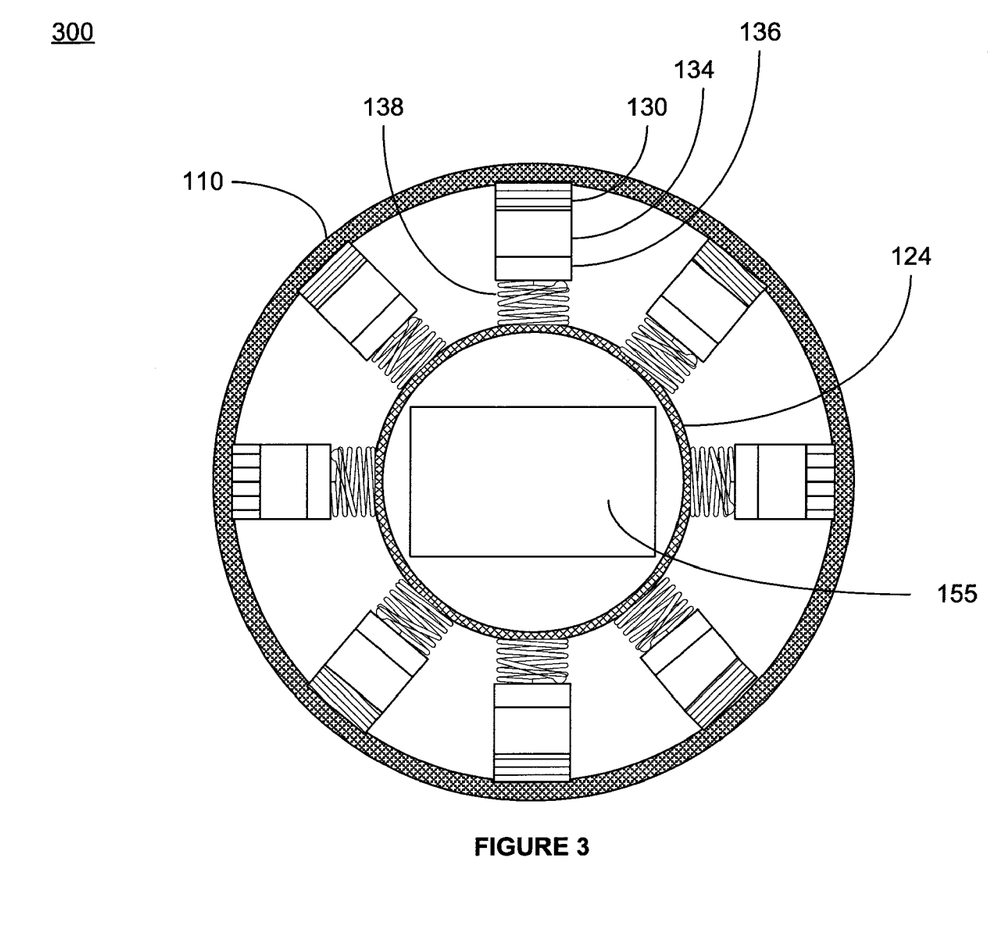
FIG. 3 shows a radial cross-section of an embodiment of the present invention.

Turning now to FIG. 3, FIG. 3 shows a radial cross-section of an embodiment of the present invention 300. Although the cross-section view shown in FIG. 3 corresponds to the permanent magnet embodiment of the present invention shown in FIG. 1, it may also represent the embodiment shown in FIG. 2, as well as other embodiments. FIG. 3 shows a pipe wall 110 and a center section 124 of an inspection pig containing an instrumentation pack 155. A plurality of magnetic field producing assemblies comprising brushes 130, permanent magnets 134, ferromagnetic connectors 136 and springs 138 are radially positioned between the inspection pig center section 124 and the pipe wall 110. The Barkhausen noise sensors and sensor positioning springs (142 and 140 in FIGS. 1 and 2) associated with each of the magnetic field producing assemblies are not shown in the vicinity of the front brushes 130 in FIG. 3 for clarity. The size and number of Barkhausen sensors may be tailored to a particular defect type that is being investigated. Many small sensors could be incorporated to detect small areas of surface stress, while fewer but larger sensors would provide the benefit of improved signal-to-noise ratios on defects of larger size. Furthermore, if the method was focused on detecting only stresses from bends in a pipe wall 110, each sensor could be designed to detect Barkhausen noise over a radial angle of from 45 to 90 degrees of the circumference of the pipe wall 110. Another feature of the present method for detecting stress is that it can be enhanced by making trending measurements over a period of time, providing detection of changes in Barkhausen noise signals that have higher detection sensitivity than absolute measurements.

Figure 4:
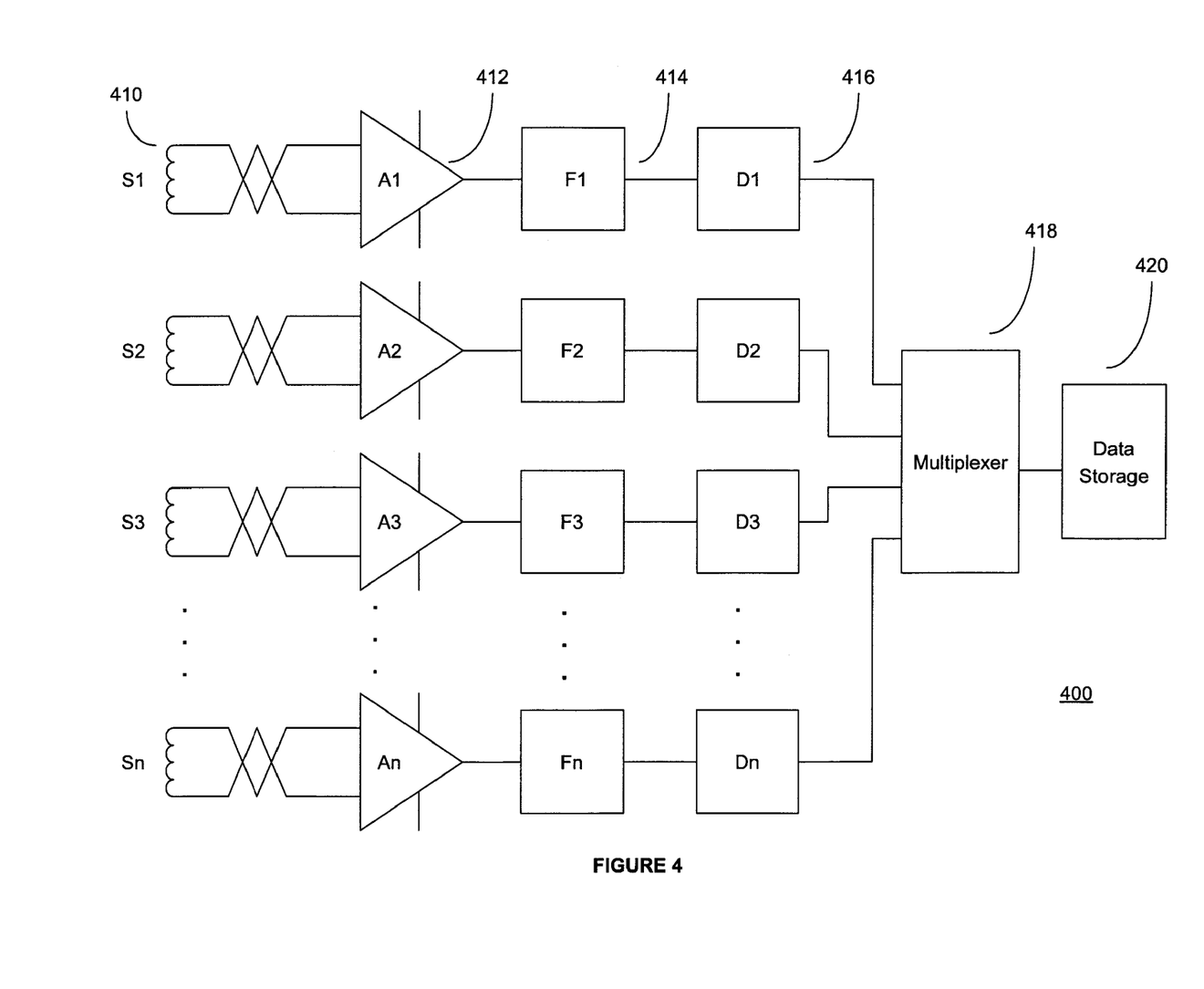
FIG. 4 shows a block diagram of an embodiment the instrumentation circuits of the present invention.

Turning now to FIG. 4, FIG. 4 shows a block diagram 400 of an embodiment the instrumentation circuits of the present invention. A plurality of inductive or other type of magnetic field sensors 410 for reading Barkhausen noise signals are connected to inputs of amplifiers 412 for amplifying the signals from the sensors 410. Outputs of the amplifiers 412 are connected to inputs of filters 414 for limiting the signal bandwidth of the Barkhausen noise signals at the outputs of the filters 414. Inputs of detectors 416 are connected to the outputs of the filters 414 to provide detected signals from the outputs of the detectors 416 to inputs to a multiplexer 418. As the multiplexer 418 reads the detected signals from the detectors 416, the multiplexed detected signals from the output of the multiplexer 418 are provided to a data storage device 420, for storing the multiplexed Barkhausen noise data. The stored detected Barkhausen noise signals in the data storage device 420 are subsequently analyzed and interpreted in relation to corresponding positions of the inspection pig within the pipeline for determining stresses and corresponding stress locations in the pipeline walls. Instead of measuring the intensity or energy of the detected Barkhausen signals, other embodiments of signal analysis involve analyzing the height of individual Barkhausen pulses (Pulse Height Analysis) or counting individual pulses to relate the Barkhausen signals to stress.

Although the present invention has been described in detail with reference to certain preferred embodiments, it should be apparent that modifications and adaptations to those embodiments might occur to persons skilled in the art without departing from the spirit and scope of the present invention.

The invention claimed is:

1. A method for in-line stress measurement of pipeline wall surfaces by continuous Barkhausen noise detection, comprising the steps of:
   creating one or more magnetic fields circumferentially positioned in a pipeline wall aligned and moving parallel with an axis of the pipeline;
   sensing Barkhausen noise signals by one or more magnetic sensors located at one or more surfaces of the pipeline wall near one or more transition zones created by the one or more magnetic fields where there are strong magnetic field gradients;
   amplifying, filtering, detecting, multiplexing and storing the magnetically sensed Barkhausen noise created by the moving magnetic fields; and
   analyzing and interpreting the stored Barkhausen noise signals in relation to corresponding positions of the inspection pig within the pipeline for determining stress magnitude and corresponding locations of stress in the pipeline wall.

2. The method of claim 1, wherein the step of creating one or more magnetic fields comprises:
   positioning one or more magnets each having a north pole and a south pole on the circumference of a cylindrically-shaped inspection pig movably contained within a pipeline;
   aligning one or more magnetic fields produced by the one or more magnets for producing magnetic fields in a wall of the pipeline parallel to a longitudinal axis of the inspection pig and the pipeline; and
   moving the inspection pig along the longitudinal axis of the pipeline.

3. The method of claim 2, wherein the step of sensing Barkhausen noise signals comprises locating one or more magnetic sensors at transition zones adjacent to the poles of the one or more magnets and outside the one or more magnetic fields where there are strong magnetic field gradients in the pipeline wall for detecting Barkhausen noise in the pipeline wall.

4. The method of claim 3, wherein the step of amplifying, filtering, detecting, multiplexing and storing comprises:
   connecting the one or more magnetic noise sensors to instrumentation circuits in an instrumentation pack contained within the inspection pig; and
   sensing Barkhausen noise signals for determining stress in the pipeline wall and storing the noise signals in the instrumentation pack as the inspection pig is caused to transit the pipeline along the longitudinal axis of the pipeline.

5. The method of claim 4, wherein the step of connecting the one or more magnetic noise sensors comprises:
   connecting the one or more magnetic noise sensors to input terminals of one or more amplifiers in the instrumentation pack;
   connecting output terminals of the one or more amplifiers to input terminals of one or more filters in the instrumentation pack;
   connecting output terminals of the one or more filters to input terminals of one or more detector circuits in the instrumentation pack;
   connecting output terminals of the one or more detector circuits to input terminals of a multiplexer in the instrumentation pack; and
   connecting an output terminal of the multiplexer to a data storage device in the instrumentation pack for storing multiplexed Barkhausen noise data.

6. The method of claim 2, wherein the step of positioning one or more magnets is selected from the group consisting of positioning one or more permanent magnets and positioning one or more DC electromagnets magnets energized by a battery pack.

7. The method of claim 2, wherein the step of positioning one or more magnets further comprises positioning one or more magnets in close proximity to a wall of the pipeline.

8. The method of claim 2, wherein the steps of positioning one or more magnets and aligning one or more magnetic fields are included in an existing MFL inspection pig.

9. The method of claim 3, further comprising the step of generating Barkhausen magnetic transitions in the transition zones in the pipeline wall as the inspection pig is caused to transit the pipeline.

10. The method of claim 3, wherein the step of locating one or more magnetic sensors further comprises locating a multitude of small magnetic sensors for detecting small areas of pipe wall stress.

11. The method of claim 3, wherein the step of locating one or more magnetic sensors further comprises locating a small number of large magnetic sensors providing improved signal-to-noise ratios for detecting large areas of pipe wall stress.

12. The method of claim 3, wherein the step of locating one or more magnetic sensors further comprises locating one or more magnetic sensors over a radial angle of from 45 to 90 degrees of the circumference of the inspection pig for detecting only stresses due to bends in the pipeline wall.

13. The method of claim 1, further comprising the step of enhancing detection of pipeline stress by making trending measurements of stored Barkhausen noise signals over a period of time for providing higher detection sensitivity than single absolute measurements of Barkhausen noise signals.

14. A system for in-line stress measurement of pipeline wall surfaces by continuous Barkhausen noise detection, comprising:
    means for creating one or more magnetic fields circumferentially positioned in a pipeline wall aligned and moving parallel with an axis of the pipeline;
    means for sensing Barkhausen noise signals by one or more magnetic sensors located at one or more surfaces of the pipeline wall in one or more transition zones created by the one or more magnetic fields where there are strong magnetic field gradients;
    means for amplifying, filtering, detecting, multiplexing and storing the magnetically sensed Barkhausen noise created by the moving magnetic fields; and
    means for analyzing and interpreting the stored Barkhausen noise signals in relation to corresponding positions of the inspection pig within the pipeline for determining stress magnitude and corresponding locations of stress in the pipeline wall.

15. The system of claim 14, wherein the means for creating one or more magnetic fields comprises:
    one or more magnets each having a north pole and a south pole positioned on the circumference of a cylindrically-shaped inspection pig movably contained within a pipeline;
    one or more magnetic fields produced by the one or more magnets for producing magnetic fields in a wall of the pipeline aligned parallel to a longitudinal axis of the inspection pig and the pipeline; and
    means for moving the inspection pig along the longitudinal axis of the pipeline.

16. The system of claim 15, wherein the means for sensing Barkhausen noise signals comprises one or more magnetic sensors located at transition zones adjacent to the poles of the one or more magnets and outside the one or more magnetic fields where there are strong magnetic field gradients in the pipeline wall for detecting Barkhausen noise in the pipeline wall.

17. The system of claim 16, wherein the means for amplifying, filtering, detecting, multiplexing and storing comprises:
    one or more magnetic noise sensors connected to instrumentation circuits in an instrumentation pack contained within the inspection pig; and
    Barkhausen noise signals sensed for determining stress in the pipeline wall and stored in the instrumentation pack as the inspection pig is caused to transit the pipeline along the longitudinal axis of the pipeline.

18. The system of claim 17, wherein the one or more magnetic noise sensors connected to the instrumentation circuits comprises:
    the one or more magnetic noise sensors connected to input terminals of one or more amplifiers in the instrumentation pack;
    output terminals of the one or more amplifiers connected to input terminals of one or more filters in the instrumentation pack;
    output terminals of the one or more filters connected to input terminals of one or more detector circuits in the instrumentation pack;
    output terminals of the one or more detector circuits connected to input terminals of a multiplexer in the instrumentation pack; and
    an output terminal of the multiplexer connected to a data storage device in the instrumentation pack for storing multiplexed Barkhausen noise data.

19. The system of claim 15, wherein the means for positioning one or more magnets is selected from the group consisting of means for positioning one or more permanent magnets and means for positioning one or more DC electromagnets magnets energized by a battery pack.

20. The system of claim 15, wherein the one or more magnets are positioned in close proximity to a wall of the pipeline.

21. The system of claim 15, wherein the positioned one or more magnets and aligned one or more magnetic fields are included in an existing MFL inspection pig.

22. The system of claim 16, further comprising the one or more magnets for generating Barkhausen magnetic transitions in the transition zones in the pipeline wall as the inspection pig is caused to transit the pipeline.

23. The system of claim 16, wherein the one or more magnetic sensors further comprises a multitude of small magnetic sensors for detecting small areas of pipe wall stress.

24. The system of claim 16, wherein the one or more magnetic sensors further comprises a small number of large magnetic sensors providing improved signal-to-noise ratios for detecting large areas of pipe wall stress.

25. The system of claim 16, wherein the one or more magnetic sensors further comprises one or more magnetic sensors located over a radial angle of from 45 to 90 degrees of the circumference of the inspection pig for detecting only stresses due to bends in the pipeline wall.

26. The system of claim 14, further comprising enhanced detection by trending measurements of stored Barkhausen noise signals over a period of time for providing higher detection sensitivity than single absolute measurements of Barkhausen noise signals.

27. A system for in-line stress measurement of pipeline wall surfaces by continuous Barkhausen noise detection, comprising:
    an MFL inspection pig including means for creating one or more magnetic fields circumferentially positioned in a pipeline wall aligned and moving parallel with an axis of the pipeline as the MFL inspection pig transits the pipeline;
    means for sensing Barkhausen noise signals by one or more magnetic sensors located at one or more surfaces of the pipeline wall in one or more transition zones created by the one or more magnetic fields where there are strong magnetic field gradients created by the MFL inspection pig;
    means for amplifying, filtering, detecting, multiplexing and storing the magnetically sensed Barkhausen noise created by the moving magnetic fields of the MFL inspection pig; and
    means for analyzing and interpreting the stored Barkhausen noise signals in relation to corresponding positions of the MFL inspection pig within the pipeline for determining stress magnitude and corresponding locations of stress in the pipeline wall.

28. The system of claim 27, wherein the MFL inspection pig comprises:
one or more magnets each having a north pole and a south pole positioned on the circumferential surface of the MFL inspection pig movably contained within a pipeline;
one or more magnetic fields produced by the one or more magnets for producing magnetic fields in a wall of the pipeline aligned parallel to a longitudinal axis of the MFL inspection pig and the pipeline; and
means for moving the MFL inspection pig along the longitudinal axis of the pipeline.

29. The system of claim 27, wherein:
the means for sensing Barkhausen noise signals comprises one or more magnetic sensors located at transition zones adjacent to the poles of the one or more magnets and outside the one or more magnetic fields where there are strong magnetic field gradients in the pipeline wall for detecting Barkhausen noise in the pipeline wall;
the means for amplifying, filtering, detecting, multiplexing and storing comprises one or more magnetic noise sensors connected to instrumentation circuits in an instrumentation pack contained within the MFL inspection pig; and
the Barkhausen noise signals sensed for determining stress in the pipeline wall and stored in the instrumentation pack as the MFL inspection pig is caused to transit the pipeline along the longitudinal axis of the pipeline.

30. The system of claim 27, further comprising enhanced detection by trending measurements of stored Barkhausen noise signals over a period of time for providing higher detection sensitivity than single absolute measurements of Barkhausen noise signals.

* * * * *